United States Patent [19]
Regnier et al.

[11] Patent Number: 5,283,246
[45] Date of Patent: Feb. 1, 1994

[54] TRIMETAZIDINE COMPOUNDS

[75] Inventors: Gilbert Regnier; Jean-Paul Vilaine, both of Chatenay Malabry; Nicole Villeneuve, Rueil Malmaison; Jean-Pierre Bidouard, Chilly Mazarin; Jean-Pierre Iliou, Puteaux; Albert Lenaers, Triel sur Seine, all of France

[73] Assignee: Adir et Compagnie, Courbevoie, France

[21] Appl. No.: 946,933

[22] Filed: Sep. 17, 1992

[30] Foreign Application Priority Data

Sep. 18, 1991 [FR] France ................. 91 11469

[51] Int. Cl.$^5$ ............... A61K 31/495; C07D 295/088; C07D 295/092; C07D 405/06
[52] U.S. Cl. .................... 514/255; 514/253; 544/376; 544/398; 544/399; 544/401
[58] Field of Search ............. 544/376, 398, 399, 401; 514/253, 255

[56] References Cited

U.S. PATENT DOCUMENTS 4,100,285 7/1978 Murai et al. ............. 544/398
4,728,650 3/1988 Eziri et al. ............. 544/376

FOREIGN PATENT DOCUMENTS 1187706 4/1970 United Kingdom.

OTHER PUBLICATIONS

Erizi et al., Chemical Abstracts, vol. 109, No. 22844 (1988) (Abstract for WO 87 05020, Aug. 27, 1987).

Primary Examiner—Emily Bernhardt
Attorney, Agent, or Firm—Gordon W. Hueschen

[57] ABSTRACT

The compounds are substituted trimetazidine useful for the treatment of ischaemic pathologies and peripheral vascular pathology.

A compound disclosed is 4-(2,3,4-trimethoxybenzyl)-1-[3-(4-hydroxy-2,3,5-trimethylphenoxy)propyl]piperazine.

15 Claims, No Drawings

TRIMETAZIDINE COMPOUNDS

The present invention relates to new trimetazidine compounds, a process for their preparation and pharmaceutical compositions containing them.

It relates more especially to trimetazidine compounds of

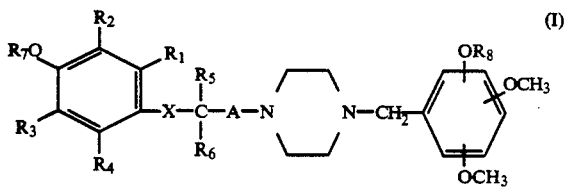

wherein:
- $R_1$ and $R_4$, which are the same or different, each represents a hydrogen atom, a methyl radical or a methoxy radical;
- $R_2$ and $R_3$, which are the same or different, each represents a straight-chain or branched alkyl or alkoxy radical each having from 1 to 6 carbon atoms;
- $R_5$ and $R_6$, which are the same or different, each represents a hydrogen atom or a methyl radical;
- $R_7$ represents a hydrogen atom or an acyl radical of formula $R'_7$—CO— wherein $R'_7$ represents a straight-chain or branched alkyl radical having from 1 to 5 carbon atoms, or a phenyl or phenylmethyl radical each of which is optionally substituted in the benzene ring by a straight-chain or branched alkyl or alkoxy radical each having from 1 to 5 carbon atoms;
- $R_8$ represents a hydrogen atom or a straight-chain or branched alkyl radical containing from 1 to 5 carbon atoms;
- X represents a single bond, an oxygen atom or a sulphur atom, and
- when X represents an oxygen atom or a sulphur atom, $R_1$ and $R_5$ may (in addition to the meaning already given above) together represent a $CH_2$ group, and
- A represents a straight-chain or branched hydrocarbon chain containing from 2 to 6 carbon atoms that is optionally substituted by a hydroxy radical.

When A contains a chiral carbon atom, the corresponding compounds may exist in the form of enantiomers or diastereoisomers which also form part of the present invention.

The closest prior art to the present invention is illustrated:

by the European Patent Application published under the number 0202580 which relates, inter alia, to 3,4-dihydrobenzopyran compounds of which the compounds closest to the present invention have the formula

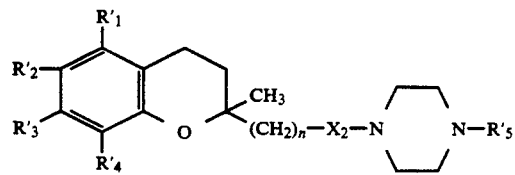

wherein $R'_1$ and $R'_4$ are hydrogen or lower alkyl, $R'_2$ is hydrogen, lower alkoxy or lower alkenyloxy, but is never hydroxy $R'_3$ is hydrogen, lower alkyl or lower alkoxy, n is zero, one or two, $X_2$ may be, inter alia, $CH_2$, $R'_5$ may be a benzyl radical polysubstituted, inter alia, by lower alkoxy radicals;

such compounds inhibit peptic ulcers and have an antitussive and/or anti-expectorant activity; and by the PCT Patent Application published under the number WO 87/05020 on 27th Aug. 1987, which relates to 3,4-dihydro-2H-benzopyran compounds of formula:

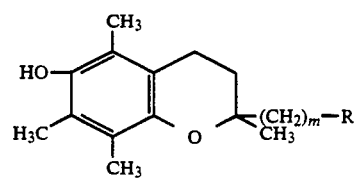

wherein:

m represents 1, 2 or 3 and

R represents, inter alia,

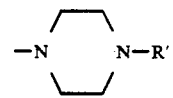

R' being, inter alia, an optionally substituted aralkyl radical;

it being possible for the said compounds to be used as medicaments.

Structural modifications have resulted in the compounds of formula I of the present invention, which have a particularly valuable antihypoxic and anti-ischaemic activity.

The present invention also relates to a process for the preparation of compounds of the general formula I which is characterized in that:

a compound of the general formula II:

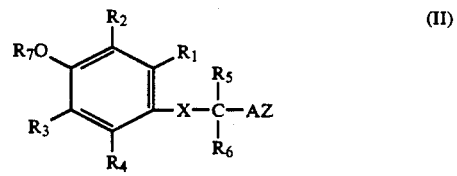

wherein:
- $R_1$, $R_2$, $R_3$, $R_4$, $R_5$, $R_6$, $R_7$ and A have the meanings given hereinbefore, and
- Z represents a halogen atom, such as a chlorine or bromine atom, or a tosyloxy radical, is reacted with a compound of formula III:

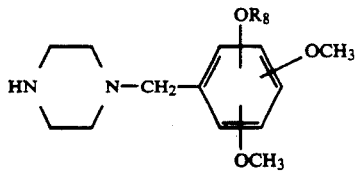

wherein $R_8$ has the meaning given hereinbefore and, when $R_7$ represents an acyl radical, the product of the reaction may, if desired, be hydrolyzed to yield the corresponding hydroxylated compound.

In some cases, the reaction of compounds II and III can be carried out without solvent, with an excess of compound III which acts as an acceptor of the acid formed during the course of the reaction, at a temperature of from 80 to 180° C.

In most cases, the above reaction is carried out in a solvent selected from the aromatic hydrocarbons, such as, for example, toluene and xylene, and polar aprotic solvents such as methyl cyanide, dimethylformamide and dimethyl acetamide, operating at a temperature of from 80 to 130° C., in the presence of an acceptor of the acid ZH formed during the course of the reaction—that acceptor being sodium or potassium carbonate, triethylamine, or an excess of compound III.

The hydrolysis of the product of the reaction when $R_7$ is an acyl group is carried out by heating for a few hours in a basic medium or in a diluted acidic medium, in a low-molecular-weight alcohol, depending on the nature of R.

The products so obtained are purified by crystallization of their salts in polar solvents or, more generally, by flash chromatography on a silica support (35–70 μ) eluting with appropriate systems such as: $CH_2Cl_2/CH_3OH$, $CH_3COOC_2H_5/CH_3OH$, $CH_3COOC_2H_5$/acetone, $CH_2Cl_2/CH_3COOC_2H_5$.

The compounds of formula I can be converted into addition salts with acids, which salts, as such, form part of the invention. There may be mentioned as acids for the formation of those salts, for example, in the mineral series, hydrochloric, hydrobromic, nitric, sulphuric and phosphoric acid and, in the organic series, acetic, propionic, maleic, fumaric, tartaric, oxalic, benzoic, methanesulphonic and isethionic acid.

The compounds of the present invention have valuable pharmacological and therapeutic properties. In particular, the following has been demonstrated for those compounds:

In vitro on the one hand: their antihypoxic activity, preventing the dysfunction of the isolated hearts of rats during hypoxia reoxygenation protocols, and their vascular relaxing activity; on the other hand : their capacity to protect cardiac cells from oxidative necrosis and to protect human LDLs (low-density lipoproteins ensuring the transport of cholesterol) from oxidative modifications induced by copper,

In vivo their anti-ischaemic activity during myocardial ischaemia protocols induced by coronary stenosis in pigs.

The above properties enable the compounds of the present invention to be used as medicaments in the preventative and curative treatment of ischaemic pathologies, especially in the cardiovascular field: angina of the chest, myocardial infarction, and the sequelae of ischaemic cardiopathies (rhythm disorder, cardiac insufficiency) and peripheral vascular pathology.

The compounds of the present invention may also be used in the cerebral field, especially for the treatment of cerebral vascular accident and manifestations of deficiency associated with chronic cerebral circulatory disorders; in the ophthalmology field : especially for the treatment of retinal disorders of vascular origin; and in neurosensory disorders of ischaemic origin.

The antioxidant properties of the compounds also makes them valuable for the prevention or treatment of pathologies in which lipidic peroxidation plays an initiating and/or aggravating role : such as, for example, in addition to the ischaemic cardiopathies already mentioned, atherosclerotic vascular lesions especially within the context of dyslipidaemias, (the oxidative modifications of LDLs now appearing, in fact, to constitute a significant mechanism in the formation and extension of atherosclerotic vascular lesions), the reperfusion of organs, including transplanted organs, ischaemic, traumatic or degenerative pathologies of the central or peripheral nervous system, acute or chronic inflammatory disorders and autoimmune disorders.

The present invention also relates to pharmaceutical compositions comprising as active ingredient a compound of formula I or a physiologically tolerable salt thereof, mixed with or in association with one or more appropriate pharmaceutical excipients.

The so-obtained pharmaceutical compositions are generally presented in dosage form. They may, for example, be in the form of tablets, dragees, capsules, suppositories or injectable or drinkable solutions, and may be administered by the oral, rectal or parenteral route.

The dosage may vary, especially in accordance with the age and weight of the patient, the route of administration, the nature of the disorder and associated treatments, and ranges from 1 to 200 mg of active ingredient from 2 to 3 times per day.

The following Examples illustrate the invention.

The melting points are determined using a capillary tube (cap) or a Kofler hot plate (K).

EXAMPLE 1

4-(2,3,4-trimethoxybenzyl)-1-[3-(4-hydroxy-2,3,5-trimethyl phenoxy) propyl]piperazine:

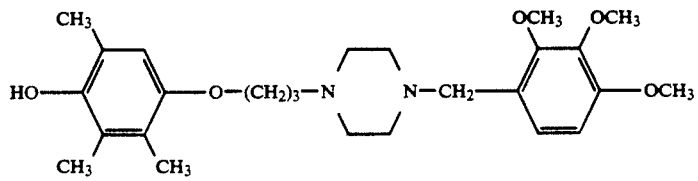

A solution of 8.4 g of 3-(4-acetoxy-2,3,5-trimethylphenoxy)-1-bromopropane melting (K) at 51° C. and 17.6 g of 1-(2,3,4-trimethoxybenzyl)piperazine in 200 ml of acetonitrile is heated at reflux for 15 hours in the presence of 0.2 g of potassium iodide. When the reaction is complete, the solvent is evaporated off under reduced pressure and the oily residue obtained is purified by flash chromatography on 600 g of silica using $CH_2Cl_2/CH_3OH$ (96:4) as eluant. 11 g of 4-(2,3,4-trimethoxybenzyl)-1-[3-(4-acetoxy-2,3,5-trimethylphenoxy)-propyl]piperazine, melting (K) at 95° C., are obtained.

That compound is hydrolyzed by heating at reflux for 1 hour in a solution of 200 ml of methanol containing 23.1 ml of normal sodium hydroxide solution. After removal of the solvent by evaporation, the residue is taken up in 200 ml of ether and the solution is washed several times with water. After evaporation, 9.6 g of an oily product are obtained which are converted in ethanol into the difumarate. Ultimately 12.5 g of 4-(2,3,4-trimethoxybenzyl)-1-[3-(4-hydroxy-2,3,5-trimethylphenoxy) propyl]piperazine difumarate are obtained, in the form of crystals that melt (K) at 2000° C.

EXAMPLE 2

4-(2,3,4-trimethoxybenzyl)-1-[3-(4-hydroxy-3,5-di-tert.-butylphenylthio)-3,3-dimethylpropyl]piperazine:

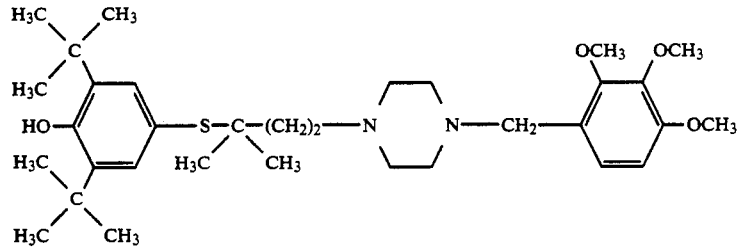

A solution of 9 g of 3-(4-hydroxy-3,5-di-tert.-butylphenylthio)-3,3-dimethyl-1-tosyloxypropane, melting (K) at 94° C., and 10.07 g of 1-(2,3,4-trimethoxybenzyl)-piperazine in 200 ml of acetonitrile is heated at reflux for 15 hours in the presence of 0.2 g of potassium iodide.

When the reaction is complete, the solvent is evaporated off under reduced pressure, and the oily residue is taken up in 150 ml of $CH_2Cl_2$, washed with water and evaporated. An oily product is obtained which is purified by flash chromatography on 300 g of silica using $CHCl_2$/acetone (90:10) as eluant. Ultimately 3 g of product are obtained which are converted in ethanol into the difumarate. Finally, 3 g of 4-(2,3,4-trimethoxybenzyl)-1-[3-(4-hydroxy-3,5-di-tert.-butylphenyl thio)-3,3-dimethylpropylpiperazine difumarate are obtained, in the form of crystals melting (K) at 2040° C.

EXAMPLES 3 TO 22

The following compounds were prepared by proceeding as described in one and/or the other of the Examples above:

3) 4-(2,3,4-trimethoxybenzyl)-1-[3-(4-hydroxy-3,5-di-tert.-butyl phenoxy) propyl]piperazine, m.p. (cap) of the corresponding dihydrochloride : 250°-254° C.
4) 4-(2,3,4-trimethoxybenzyl)-1-[3-(4-hydroxy-3,5-di-tert.-butylphenyl)propyl]piperazine, m.p. (cap) of the corresponding dihydrochloride: 225°-228° C.
5) 4-(2,3,4-trimethoxybenzyl)-1-[3-(4-hydroxy-3,5-di-tert.-butylphenoxy)-2-hydroxypropyl]piperazine, m.p. (K) of the corresponding dihydrochloride: 208° C.
6) 4-(2,3,4-trimethoxybenzyl)-I-[3-(4-hydroxy-3,5-di-tert.-butylphenylthio)-2-hydroxypropyl]piperazine, m.p. (K) of the corresponding difumarate : 178° C.
7) 4-(2,3,4-trimethoxybenzyl)-I-[3-(4-hydroxy-3,5-di-tert.-butylphenylthio)propyl]piperazine, m.p. (K) of the corresponding difumarate: 192° C.
8) 4-(2,3,4-trimethoxybenzyl)-1-[5-(4-hydroxy-3,5-di-tert.-butylphenoxy)pentyl]piperazine, m.p. (K) of the corresponding difumarate: 210° C.
9) 4-(2,3,4-trimethoxybenzyl)-1-[5-(4-hydroxy-3,5-di-tert.-butylphenylthio)pentyl]piperazine, m.p. (K) of the corresponding difumarate : 190° C.
10) 4-(2,3,4-trimethoxybenzyl)-1-[5-(4-hydroxy-2,3,5-trimethylphenoxy)pentyl]piperazine, m.p. (K) of the corresponding difumarate: 176° C.
11) 4-(2,3,4-trimethoxybenzyl)-1-[3-(4-hydroxy-2,3,5-trimethylphenoxy)-2-hydroxypropyl]piperazine, m.p. (K) of the corresponding difumarate: 192° C.
12) 4-(2,3,4-trimethoxybenzyl)-1-[3-(4-hydroxy-3,5-di-tert.-butylphenylthio)-2,2-dimethylpropyl]piperazine, m.p. (K) of the corresponding difumarate: 180° C.
13) 4-(2,3,4-trimethoxybenzyl)-1-[3-(4-hydroxy-2,3,5-trimethylphenylthio)-2-hydroxypropyl)piperazine, m.p. (K) of the corresponding difumarate: 158° C.
14) 4-(2,3,4-trimethoxybenzyl)-1-[3-(4-hydroxy-2,3,5-trimethylphenylthio)propyl]piperazine, m.p. (K) of the corresponding dihydrochloride.0.7 $H_2O$:200° C.
15) 4-(3,4,5-trimethoxybenzyl)-1-[3-(4-hydroxy-2,3,5-trimethylphenoxy)propyl]piperazine,
16) 4-(2,4,6-trimethoxybenzyl)-I-[3-(4-hydroxy-2,3,5trimethylphenoxy)propyl)piperazine.
17) 4-(2,3,4-trimethoxybenzyl)-I-[(5-hydroxy-2,4,6,7-tetramethyl-2,3-dihydrobenzofuran-2-yl)propyl]piperazine, of which the dihydrochloride is an amorphous product.
18) 4-(2,3,4-trimethoxybenzyl)-1-[(5-hydroxy-2,4,6,7-tetramethyl-2,3-dihydrobenzothien-2-yl)methyl]piperazine.
19) 4-(2-hydroxy-3,4-dimethoxybenzyl)-1-[3-(4-hydroxy-2,3,5-trimethylphenylthio)-2-hydroxypropyl]piperazine.
20) 4-(2,3,4-trimethoxybenzyl)-1-13-(4-acetoxy-2,3,5-trimethylphenylthio)-2-hydroxypropyl]piperazine.
21) (R-)-4-(2,3,4-trimethoxybenzyl)-1-[3-(4-hydroxy-2,3,5-trimethylphenylthio)-2-hydroxypropyl]piperazine, and its corresponding bis-methanesulphonate, melting point (K)=164° C. and $[\alpha]_D^{21} = -19.9°$ (c=1%, $C_2H_5OH$).
22) (S+)-4-(2,3,4-trimethoxybenzyl)-1-[3-(4-hydroxy-2,3,5-trimethylphenylthio)-2-hydroxypropyl)piperazine, and its corresponding bis-methanesulphonate, melting point (K)=165° C. and $[\alpha]_D^{21} = +21.1°$ (c=1%, $C_2H_5OH$).

Some of the halogenated or tosyloxy starting materials used to synthesize the compounds of formula I are described in published European Patent Application No. 0 433 167 A1, pages 10 and 11 (Corresponding U.S. patent is U.S. Pat. No. 5,126,356, issued Jun. 30, 1992). The others are listed below.

| COMPOUNDS | PHYSICAL CONSTANTS |
|---|---|
| CH₃COO-[2,6-di-CH₃, 3-CH₃ phenyl]-O-(CH₂)₅-Br | liquid, $n_D^{18} = 1.517$ |
| OH-[2,6-di-CH₃, 3-CH₃ phenyl]-S-CH₂-CH(OH)-CH₂-Cl | m.p. (K): 76° C. |
| HO-[3,5-di-C(CH₃)₃ phenyl]-S-C(CH₃)₂-(CH₂)₂-O tosyl | m.p. (K): 94° C. |
| HO-[3,5-di-C(CH₃)₃ phenyl]-S-CH₂-C(CH₃)₂-CH₂-O tosyl | m.p. (K): 77° C. |
| HO-[3,5-di-C(CH₃)₃ phenyl]-S-CH₂-CH(OH)-CH₂-Cl | m.p. (K): 68° C. |

All of the above compounds were prepared as mentioned on pages 10 and 11 of European Patent Application No. 0 433 167 A1 (Corresponding U.S. patent is U.S. Pat. No. 5,126,356, issued Jun. 30, 1992) for the preparation of analogous compounds.

EXAMPLE 23

PHARMACOLOGICAL STUDY

The cardiac protecting effect of the compounds of the present invention was demonstrated on the one hand in vitro: on the isolated hearts of rats subjected to a hypoxia reoxygenation cycle, as well as on cardiac cells of rats subjected to oxidative necrosis, and on the other hand in vivo: during myocardial ischaemic episodes in pigs induced by coronary stenosis.

In addition, the following properties of the compounds were demonstrated in vitro : their vascular relaxing activity on isolated vessels of rats, and their LDL-protecting effect on human LDLs subjected to an oxidative modification induced by copper sulphate.

A—IN VITRO STUDY

1. Materials and Methods a) Hypoxia Reoxygenation on the Isolated Heart of a Rat The hearts of male Wistar rats (325-375 g—Charles River breed) anaesthetized by the intraperitoneal route with sodium pentobarbital (30 mg/kg) are removed after the injection of heparin i.v. (1 ml/kg) and rapidly perfused by the Langendorff technique at a constant pressure of 76 mmhg and stimulated electrically at 5 Hz. The isovolumetric contractions are recorded by way of a small polyethylene balloon connected to a pressure sensor (P23-Gould) introduced into the left ventricle and inflated so as to obtain a diastolic pressure of approximately 10 mmhg. The physiological solution used, maintained at 37° C., has the following composition (mM): NaCl 118; KCl 4.7; KH₂PO₄ 1.2; MgCl₂ 1.2; CaCl₂ 1.3; NaHCO₃ 25; glucose 8, pH 7.4/95% O₂+5% CO₂.

After a period of stabilization of from 15 to 30 minutes, the heart is subjected to hypoxia for 60 minutes (effected with 95% N₂ and 5% CO₂; $P_{O_2} < 40$ mmHg), followed by reoxygenation for 30 minutes; the compound is added to the incubation medium 15 minutes before and during the period of hypoxia.

b) Oxidative Necrosis of Cardiac Cells

The cardiac cells of newborn rats are used between the 5th and 6th days after placing in culture. Oxidative necrosis is induced by the free radical-producing enzymatic system hypoxanthine (HX, 1 -mm) and xanthineoxidase (XO, 10 mU/ml). The necrosis is evaluated 4 hours after the addition of XO/HX by measuring by spectrophotometry the cytosolic α-hydroxybutyrate dehydrogenase (a-HBDH) activity liberated in the supernatant. The cells are treated with the test compounds 16 hours and 1 hour before the beginning of the experiment after renewing the medium. At the beginning of the experiment, the treatment is carried out again one last time.

c) Study on Isolated Vessels

The thoracic aorta of Wistar rats (325–375 g) that have been anaesthetized by the intraperitoneal route with sodium pentobarbital (30 mg/kg) is removed and dissected into rings 3 mm in length; the endothelium is removed by gentle abrasion using a piece of wood. Each ring is connected to a Statham pressure sensor (UC2-Gould). The initial pressure applied is 2.5 g. The physiological solution used, maintained at 37° C., has the following composition (mM): NaCl 112; KCl 5; $KH_2PO_4$ 1; $MgSO_4$ 1.2; $CaCl_2$ 2.5; $NaHCO_3$ 25; glucose 11.; EDTA 0.026. After a stabilization period of 90 minutes, the aorta rings are subjected to a hyperpotassic medium (80 MM KCl and 37 mM NaCl). When the contraction is stable, cumulative concentrations of compound are added to the medium every 15 minutes. The relaxation values obtained enable calculation of the $IC_{50}$.

d) Modification of LDLs by Copper Sulphate

Human LDLs are incubated for 24 hours in the presence of copper sulphate ($5 \times 10^{-6}M$) and in the absence or presence of the compounds tested ($10^{-7}M$ to $10^{-4}M$). After incubation, the peroxidation of the LDLs is evaluated by electrophoresis on agar gel and by the formation of one of the products of lipid peroxidation malonic dialdehyde (MDA), (Parthasarathy S., Young S. G., Witztum J. L., Pittman R. C. and Steinberg, D.; J. Clin. invest. 77; 641–644, 1986).

The activity of the tested compounds is evaluated by calculating those concentrations (IC50) that reduce the production of MDA by 50% compared with control experiments in the absence of the tested compound.

2. Results a) Effects on the Isolated heart of a Rat Subjected to hypoxia Reoxygenation The compounds of Examples 1 ($3 \times 10^{-7}M$), 10 ($10^{-7}M$) and 13 ($7 \times 10^{-7}M$), in particular, reduce the developing contracture by from 35 to 58% especially at the end of 60,minutes of hypoxia, and by more than 70% at the end of 30 minutes reoxygenation (Table 1). They permit a better functional recovery of the hearts during reoxygenation of more than 70%, compared with 40% in the control experiments (Table 2).

b) Effect on the Oxidative Necrosis of Cardiac Cells

Table 3 lists the necrosis indices of cardiac cells induced by the hypoxanthine/xanthine-oxidase system alone or in the presence of increasing concentrations of the compounds of the invention.

A concentration-dependent protection against necrosis is observed. The compounds, especially of Examples 1, 3, 9 and 10, prove to be protective at a concentration of $10^{-7}M$ and above. Most of the compounds reduce the necrosis by more than 70% at a concentration of $10^{-5}M$.

c) Effect on Isolated Vessels

The compounds listed in Table 4 have a vascular relaxing activity on a contraction induced by potassium depolarization, their $IC_{50}$ being between 2 and $5 \times 10^{-6}M$.

d) Effect on the Modification of LDLs

Table 5 lists the $IC_{50}$ values, indicating the capacity to inhibit lipidic peroxidation of human LDLs induced by copper sulphate, which are situated between $3 \times 10^{-8}M$ and $3 \times 10^{-6}M$.

TABLE 1

Effect of compounds (I) on the contracture developed during the course of a hypoxia reoxygenation of the isolated hearts of rats

| | CONTRACTURE (mm Hg) | | | | |
|---|---|---|---|---|---|
| | HYPOXIA | | | REOXYGENATION | |
| COMPOUNDS | 10 min | 30 min | 60 min | 15 min | 30 min |
| Control | 23.7 ± 6.8 | 33.7 ± 8.9 | 32.3 ± 7.4 | 20.6 ± 7.8 | 12.3 ± 6.1 |
| Example 1 ($3 \times 10^{-7}$ M) | 21.0 ± 5.8 | 22.5 ± 2.5 | 21.0 ± 3.9 | 12.5 ± 5.1 | 2.5 ± 2.5 |
| Example 10 ($10^{-7}$ M) | 15.3 ± 3.7 | 16.0 ± 6.4 | 14.7 ± 4.4 | 7.3 ± 5.5 | 2.7 ± 2.7 |
| Example 13 ($7 \times 10^{-7}$ M) | 11.0 ± 4.4 | 15.0 ± 6.1 | 13.5 ± 6.3 | 6.0 ± 6.0 | 3.5 ± 3.5 |

TABLE 2

Effects of the compounds (I) on the functional recovery of isolated hearts of rats after hypoxia

| COMPOUNDS | Left ventricular pressure 30 minutes after reoxygenation (expressed as % of the initial value before hypoxia) |
|---|---|
| Control | 41.6 ± 8.8 |
| Example 1 ($3 \times 10^{-7}$ M) | 80.5 ± 15 |
| Example 10 ($10^{-7}$ M) | 75.9 ± 2.1 |
| Example 13 ($7 \times 10^{-7}$ M) | 113.7 ± 18 |

TABLE 3

Effect of compounds (I) on the oxidative necrosis of cardiac cells

| COMPOUNDS | CONTROL XO + HX | $10^{-7}$ M XO + HX | $10^{-6}$ M XO + HX | $10^{-5}$ M XO + HX |
|---|---|---|---|---|
| Example 1 | 100.0 ± 12.6 | 70.4 ± 2.5 | 55.4 ± 6.4 | 13.9 ± 5.3 |
| Example 3 | 100.0 ± 6.2 | 72.6 ± 5.7 | 16.9 ± 1.1 | 37.6 ± 2.7 |
| Example 4 | 100.0 ± 14.7 | 102.9 ± 12.0 | 22.3 ± 6.5 | 10.2 ± 3.1 |
| Example 6 | 100.0 ± 2.5 | 99.5 ± 7.5 | 7.7 ± 0.1 | 8.3 ± 1.4 |
| Example 7 | 100.0 ± 4.2 | 85.9 ± 1.7 | 19.3 ± 0.9 | 27.9 ± 3.4 |
| Example 8 | 100.0 ± 1.1 | 91.4 ± 3.1 | 21.6 ± 4.2 | 27.2 ± 2.0 |
| Example 9 | 100.0 ± 1.0 | 53.0 ± 5.5 | 15.2 ± 2.0 | 33.3 ± 6.6 |
| Example 10 | 100.0 ± 8.3 | 88.8 ± 0.4 | 18.8 ± 3.7 | 12.6 ± 1.3 |
| Example 11 | 100.0 ± 5.1 | 114.0 ± 5.2 | 70.9 ± 8.3 | 18.0 ± 2.9 |
| Example 13 | 100.0 ± 6.1 | 100.1 ± 4.8 | 64.7 ± 0.4 | 15.1 ± 0.6 |

TABLE 4

Vascular relaxing effect of compounds (I) on a rat aorta contracted by potassium (80 mM)

| COMPOUNDS | $IC_{50}$ (M) |
|---|---|
| Example 1 | $5.0 \times 10^{-6}$ |
| Example 6 | $2.7 \times 10^{-6}$ |
| Example 10 | $2.0 \times 10^{-6}$ |
| Example 13 | $4.3 \times 10^{-6}$ |

TABLE 5

Inhibiting effect of compounds (I) on the modification of human LDLs induced by copper

| COMPOUNDS | $IC_{50}$ (M) |
|---|---|
| Example 1 | $9 \times 10^{-8}$ |
| Example 2 | $3 \times 10^{-6}$ |
| Example 3 | $5 \times 10^{-7}$ |
| Example 4 | $2 \times 10^{-6}$ |
| Example 5 | $9 \times 10^{-7}$ |
| Example 6 | $3 \times 10^{-7}$ |
| Example 7 | $6 \times 10^{-7}$ |
| Example 8 | $10^{-6}$ |
| Example 9 | $8 \times 10^{-8}$ |
| Example 10 | $3 \times 10^{-8}$ |
| Example 11 | $6 \times 10^{-7}$ |
| Example 12 | $8 \times 10^{-7}$ |
| Example 13 | $7 \times 10^{-8}$ |

B—IN VIVO STUDY

1. Materials and Methods

The study is carried out on "Large White" pigs of both sexes aged 3 months and weighing 21 to 26 kg. The animals are tranquillized using midazolam (I mg/kg i.m.), then anaesthetized with sodium thiopental (8 mg/kg i.v.). The anaesthesia is maintained by a perfusion of 6 to 8 mg/kg/h.

They are immediately intubated and ventilated with a mixture of air+$O_2$.

A "T" thoracotomy is carried out by longitudinal section of the sternum and incision between the 4th and 5th rib. The heart is suspended in a pericardial cradle made by cutting and fixing the pericardium at four points to the thoracic muscles. An electromagnetic flow ring is placed around the anterior interventricular branch of the left coronary, and a small pneumatic balloon is placed immediately downstream of that ring. This assembly is for the purpose of effecting coronary stenosis by controlling the flow.

Piezoelectric crystals connected to a Triton sonomicrometer are implanted in the lower endocardium of the left ventricular wall according to a circumferential plane perpendicular to the cardiac axis. These crystals are for recording the regional myocardial contractility and endocardial ECGs in the area supplied by the stenosed coronary artery. Epicardial ECGs are also recorded in those areas by means of electrodes fixed to the myocardium.

2. Experimental Protocol

Myocardial ischaemia is effected by inflating the small balloon which induces a reduction in flow of 50 to 60 Two identical 3 minute stenoses with reproducible and reversible effects are carried out, separated by a recovery period of 55 minutes.

The treatment is administered by five minutes' perfusion by the venous route 10 minutes before the stenosis perfusion of solvent before first stenosis
perfusion of the compound or solvent before the second stenosis.

3. Parameters Measured

The regional myocardial contractility is determined by the fraction of systolic shortening of the segment lengths comprised between the piezoelectric crystals.

The hypokinesis in the ischaemic zone is expressed as a percentage variation in relation to the contractility measured in the control period.

The modification of the epicardial and endocardial ECGs in the ischaemic zone consists in a superelevation of the segment S.T. measured in millivolts (mV).

4. Results

No difference is observed in the electrocardiograms between the effects of the two coronary stenoses induced in the control group whilst a greater degradation in the regional contractility is observed during the second coronary stenosis.

By contrast, the compound of Example 10 in particular, administered by the intravenous route at a dose of 1 mg/kg before the second coronary stenosis, reduces the superelevation of the segments ST of both the epicardial and the endocardial electrocardiograms by 45% compared with the first coronary stenosis, and causes a 50% improvement in the regional contractility in the ischaemic zone compared with the effect of the first coronary stenosis (cf. Tables 6 and 7).

TABLE 6

Effect of the compound of Example 10 on the modifications of the epicardial and endocardial ECGs during myocardial ischaemia in pigs

| COMPOUND | ST superelevation (mV) epicardial ECG | | ST superelevation (mV) endocardial ECG | |
|---|---|---|---|---|
| | ST1 | ST2 | ST1 | ST2 |
| Control | 3.7 ± 0.98 | 3.16 ± 1.2 | 2.28 ± 0.48 | 2.4 ± 0.51 |
| Example 10 | 4.6 ± 1.0 | 2.5 ± 0.6 | 3.4 ± 0.4 | 1.9 ± 0.5 |

TABLE 6-continued

Effect of the compound of Example 10 on the modifications of the epicardial and endocardial ECGs during myocardial ischaemia in pigs

| COMPOUND | ST superelevation (mV) epicardial ECG | | ST superelevation (mV) endocardial ECG | |
|---|---|---|---|---|
| | ST1 | ST2 | ST1 | ST2 |
| (1 mg/kg i.v.) | | | | |

TABLE 7

Effect of the compound of Example 10 on the regional myocardial contractility of ischaemic zones in pigs

| COMPOUND | % residual myocardial contractility | |
|---|---|---|
| | ST1 | ST2 |
| Control | 33.2 ± 2.5 | 25.2 ± 3.0 |
| Example 10 (1 mg/kg/iv) | 20.4 ± 3.3 | 29.4 ± 2.6 |

C—CONCLUSION

The results reported demonstrate that the compounds of the invention have a protective effective on cardiac tissue in vitro with respect to hypoxic or oxidative stress, and in vivo with respect to an ischaemic episode, as well as vascular antispastic activities and protective effects as regards oxidative modifications of LDLs implicated in atherogenesis.

We claim:

1. A piperazine compound selected from those of the formula I:

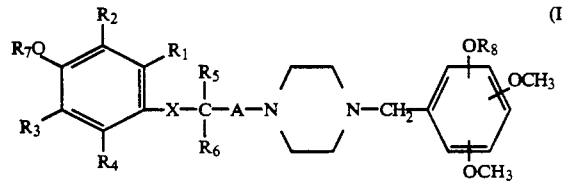

wherein:

$R_1$ and $R_4$, which are the same or different, each represents hydrogen, methyl, or methoxy;

$R_2$ and $R_3$, which are the same or different, each represents straight-chain or branched alkyl or alkoxy each having 1 to 6 carbon atoms inclusive;

$R_5$ and $R_6$, which are the same or different, each represents hydrogen or methyl;

$R_7$ represents hydrogen, of formula $R'_7$—CO— wherein $R'_7$ represents straight-chain or branched alkyl having 1 to 5 carbon atoms inclusive, or $R'_7$ represents phenyl or phenylmethyl, each of which is optionally substituted in the benzene ring by straight-chain or branched alkyl or alkoxy each having 1 to 5 carbon atoms inclusive;

$R_8$ represents hydrogen or straight-chain or branched alkyl having 1 to 5 carbon atoms inclusive;

X represents a single bond, oxygen, or sulphur, and

A represents a straight-chain or branched hydrocarbon chain having 2 to 6 carbon atoms inclusive and when A contains a chiral carbon atom, its corresponding enantiomers and diastereoisomers; and its physiologically-tolerable salts with a pharmaceutically-acceptable acid.

2. A compound of claim 1 which is selected from: 4-(2,3,4-trimethoxybenzyl)-1-[3-(4-hydroxy-2,3,5-trimethyl phenoxy)propyl]piperazine and its difumarate.

3. A compound of claim 1 which is selected from: 4-(2,3,4-trimethoxybenzyl)-1-[5-(4-hydroxy-2,3,5-trimethyl phenoxypentyl]piperazine and its difumarate.

4. A compound selected from which is: 4-(2,3,4-trimethoxybenzyl)-1-[3-(4-hydroxy-2,3,5-trimethyl phenylthio)-2-hydroxypropyl]piperazine and its difumarate.

5. A compound of claim 1 which is 4-(2,3,4-trimethoxybenzyl)-1-]3-(4-hydroxy-3,5-di-tert.-butylphenylthio)-3,3-dimethylpropyl]-piperazine or a pharmaceutically-acceptable acid addition salt thereof.

6. A compound of claim 1 which is 4-(2,3,4-trimethoxybenzyl)-1-[3-(4-hydroxy-3,5-di-tert.-butyl phenoxy)propyl]piperazine or a pharmaceutically-acceptable acid addition salt thereof.

7. A compound of claim 1 which is 4-(2,3,4-trimethoxybenzyl)-1-[3-(4-hydroxy-3,5-di-tert.-butylphenyl)-propyl]piperazine or a pharmaceutically-acceptable acid addition salt thereof.

8. A compound which is 4-(2,3,4-trimethoxybenzyl-1-[3-(4-hydroxy-3,5-di-tert.-butylphenoxy)-2-hydroxypropyl]piperazine or a pharmaceutically-acceptable acid addition salt thereof.

9. A compound which is 4-(2,3,4-trimethoxybenzyl)-1-[3-(4-hydroxy-3,5-di-tert.-butylphenylthio)-2-hydroxypropyl]piperazine or a pharmaceutically-acceptable acid addition salt thereof.

10. A compound of claim 1 which is 4-(2,3,4-trimethoxybenzyl)-1-[3-(4-hydroxy-3,5-di-tert.-butylphenylthio)propyl]piperazine or a pharmaceutically-acceptable acid addition salt thereof.

11. A compound of claim 1 which is 4-(2,3,4-trimethoxybenzyl)-1-[5-(4-hydroxy-3,5-di-tert.-butylphenoxy)pentyl]piperazine or a pharmaceutically-acceptable acid addition salt thereof.

12. A compound of claim 1 which is 4-(2,3,4-trimethoxybenzyl)-1-[5-(4-hydroxy-3,5-di-tert.-butylphenylthio)pentyl]piperazine or a pharmaceutically-acceptable acid addition salt thereof.

13. A compound of claim 1 which is 4-(2,3,4-trimethoxybenzyl)-1-[3-(4-hydroxy-3,5-di-tert.-butylphenylthio)-2,2-dimethylpropyl]-piperazine or a pharmaceutically-acceptable acid addition salt thereof.

14. A pharmaceutical composition useful in the treatment of ischemic pathologies and peripheral vascular pathology, comprising as active ingredient an effective amount of at least one compound as claimed in claim 1 together with one or more pharmaceutically-acceptable excipients.

15. A method for treating a living animal body afflicted with a condition selected from ischaemic pathologies and peripheral vascular pathology comprising the step of administering to the said body an amount of a trimetazidine compound selected from those of the formula

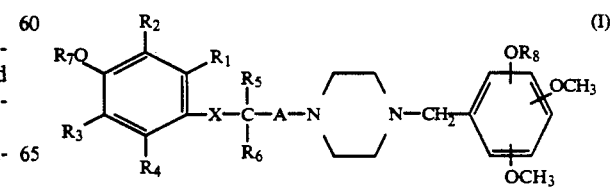

wherein:

$R_1$ and $R_4$, which are the same or different, each represents hydrogen, methyl, or methoxy;

$R_2$ and $R_3$, which are the same or different, each represents straight-chain or branched alkyl or alkoxy each having 1 to 6 carbon atoms inclusive;

$R_5$ and $R_6$, which are the same or different, each represents hydrogen or methyl;

$R_7$ represents hydrogen, acyl of formula $R'_7$—CO— wherein $R'_7$ represents straight-cain or branched alkyl having 1 to 5 carbon atoms inclusive, or $R'_7$ represents phenyl or phenylmethyl, each of which is optionally substituted in the benzene ring by straight-cain or branched alkyl or alkoxy each having 1 to 5 carbon atoms inclusive;

$R_8$ represents hydrogen or straight-chain or branched alkyl having 1 to 5 carbon atoms inclusive;

X represents a single bond, oxygen, or sulphur, and

A represents a straight-chain or branched hydrocarbon chain having 2 to 6 carbon atoms inclusive which is optionally substituted by hydroxy; and when A contains a chiral carbon atom, its corresponding enantiomers and diastereoisomers; and its physiologically-tolerable salts with a pharmaceutically-acceptable acid, which is effective for alleviation of the said condition.

* * * * *

UNITED STATES PATENT AND TRADEMARK OFFICE
CERTIFICATE OF CORRECTION

PATENT NO. : 5,283,246
DATED : Feb. 1, 1994
INVENTOR(S) : Gilbert Regnier, Jean-Paul Vilaine, Nicole Villeneuve, Jean-Pierre Bidouard, Jean Pierre Iliou, Albert Lenaers It is certified that error appears in the above-indentified patent and that said Letters Patent is hereby corrected as shown below:

Column 1, approximately line 36; "I to 5" should read
 -- 1 to 5 --.
Column 5, line 20; "2000° C." should read --200° C. --.
Column 5, line 53; "2040° C." should read -- 204° C. --.
Column 6, line 1; "-I-" should read -- -1- --.
Column 6, line 4; "-I-" should read -- -1- --.
Column 6, line 43; "-I-" should read -- -1- --.
Column 6, line 44; "2,3,5trimethylphenoxy)" should read
 -- 2,3,5-trimethylphenoxy) --.
Column 6, line 45; "-I-" should read -- -1- --.
Column 6, line 55; "-1-13-" should read -- -1-[3- --.
Column 6, line 62; "-I-" should read -- -1- --.
Column 6, line 63; "-2-hydroxypropyl)" should read
 -- -2-hydroxypropyl] --.
Column 8, approximately line 46; move "Rat" to line 4 and
 insert under "Hypoxia".
Column 8, line 53; "76 mmhg" should read -- 76 mmHg --.
Column 8, line 58; "10 mmhg." should read --10 mmHg. --.
Column 9, line 6; "-mm)" should read -- mM) --.
Column 9, line 10; "(a-HBDH)" should read -- ($\alpha$-HBDH) --.
Column 9, line 28; "11.; EDTA" should read -- 11.5; EDTA--.
Column 9, line 30; "MM" should read -- mM --.
Column 9, line 61,62; "peroxidation malonic" should read
 -- peroxidation: malonic --.
Column 9, line 66; "(IC50)" should read --($IC_{50}$) --.
Column 10, line 9; "60,minutes" should read -- 60 minutes--.
Column 11, line 47; "(I mg/kg" should read -- (1 mg/kg --.

UNITED STATES PATENT AND TRADEMARK OFFICE
CERTIFICATE OF CORRECTION

PATENT NO. : 5,283,246

DATED : Feb. 1, 1994

INVENTOR(S) : Gilbert Regnier, Jean-Paul Vilaine, Nicole Villeneuve, Jean-Pierre Bidouard, Jean-Pierre Ilou, Albert Lenaers It is certified that error appears in the above-indentified patent and that said Letters Patent is hereby corrected as shown below:

Column 12, line 24; "60 Two" should read -- 60%. Two--.
Column 12, line 28; "stenosis" should read --stenosis :--
Column 13, line 51; "hydrogen, of" should read --
    hydrogen, acyl of --.  (Cl. 1)

Column 14, line 6; "compound selected from which is" should read
    -- compound which is selected from --.  (Cl. 4, PA, P 1)
Column 14, line 11; "-1-]3-" should read -- -1-[3- --.
    (Cl. 5, old Cl. 7, R&A 5-3-93, P. 2)
Column 16, line 1; "straight-cain" should read
    -- straight-chain--.  (Cl. 15, old Cl. 6, 2nd amendment
    7-27-93, P.3,)

Signed and Sealed this

Fourth Day of October, 1994

Attest:

BRUCE LEHMAN

Attesting Officer     Commissioner of Patents and Trademarks